United States Patent [19]  [11] 4,058,611
Barreau et al.  [45] Nov. 15, 1977

[54] 1,2-DITHIOLE DERIVATIVES

[75] Inventors: Michel Barreau; Claude Cotrel, both of Paris; Claude Jeanmart, Brunoy, all of France

[73] Assignee: Rhone-Poulenc Industries, Paris, France

[21] Appl. No.: 697,157

[22] Filed: June 17, 1976

[30] Foreign Application Priority Data

June 20, 1975  France .............................. 75.19408
Apr. 15, 1976  France .............................. 76.11140

[51] Int. Cl.² ................. C07D 409/04; A61K 31/495
[52] U.S. Cl. .............................. 424/250; 260/250 B; 260/250 BN
[58] Field of Search .................... 260/250 B, 250 BN; 424/250

[56] References Cited

U.S. PATENT DOCUMENTS 3,562,253  2/1971  Twrown .......................... 260/239.3

FOREIGN PATENT DOCUMENTS 224,638  12/1972  Austria
1,136,793  12/1968  United Kingdom

OTHER PUBLICATIONS

Voronkov et al., Chemical Abstracts, vol. 76, 3730t (1972).

Primary Examiner—Donald G. Daus
Assistant Examiner—Diana G. Rivers
Attorney, Agent, or Firm—Stevens, Davis, Miller & Mosher

[57] ABSTRACT 1,2-Dithiole derivatives of the formula:

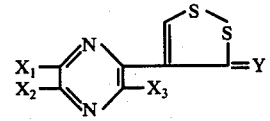

wherein $X_1$, $X_2$ and $X_3$ represent hydrogen, alkyl of 1 through 4 carbon atoms or alkoxy of 1 through 4 carbon atoms, at least one of $X_1$, $X_2$ and $X_3$ representing hydrogen, and Y represents sulphur or oxygen or the hydroxyimino radical, are new compounds useful in the treatment of bilharziasis and amoebiasis.

12 Claims, No Drawings

1,2-DITHIOLE DERIVATIVES

This invention relates to new therapeutically useful 1,2-dithiole derivatives, to processes for their preparation and pharmaceutical compositions containing them.

The new 1,2-dithiole derivatives of the present invention are those compounds of the general formula:

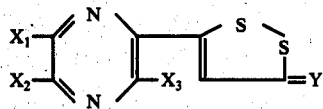

wherein the symbols $X_1$, $X_2$ and $X_3$ are the same or different and each represents a hydrogen atom, an alkyl radical containing 1 to 4 carbon atoms (preferably methyl) or an alkoxy radical containing 1 to 4 carbon atoms (preferably methoxy), at least one of the symbols $X_1$, $X_2$ and $X_3$ representing a hydrogen atom, and Y represents a sulphur or an oxygen atom or a hydroxyimino radical.

According to a feature of the present invention, the new 1,2-dithiole derivative of general formula I, wherein Y represents a sulphur atom and the other symbols are as hereinbefore defined, are prepared by the process which comprises reacting phosphorus pentasulphide with a pyrazine derivative of the general formula:

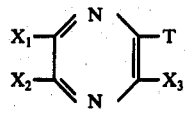

wherein $X_1$, $X_2$ and $X_3$ are as hereinbefore defined and T is a radical selected from the general formulae:

(IIIa),

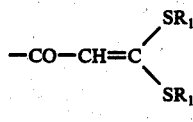
(IIIb)

and

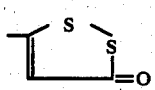
(IIIc)

wherein R represents an alkyl radical containing one to four carbon atoms, and the symbols $R_1$ are identical and represent hydrogen or alkali metal atoms or alkyl radicals containing 1 to 4 carbon atoms, or the symbols $R_1$ together form an alkylene radical containing 2 to 4 carbon atoms.

The reaction is generally effected:

i. when T represents a radical of general formula IIIa, in an organic solvent, such as toluene, benzene, a xylene or pyridine, at elevated temperature, preferably at the boiling point of the reaction mixture;

ii. when T represents a radical of general formula IIIb, in an aromatic solvent, such as toluene, benzene or a xylene, at elevated temperature, preferably at the boiling point of the reaction mixture;

iii. when T represents a radical of formula IIIc, in an organic solvent, such as toluene, dioxan or 1,2-dimethoxyethane, at a temperature of about 100° C.

The pyrazine derivatives of general formula II in which T is of general formula IIIa can be obtained by application of the method described by T. I. Fond and P. E. Spoerri, J. Amer. Chem. Soc., 74, 583 (1952).

The pyrazine derivatives of general formula II in which T is of general formula IIIb can be prepared according to one of the following methods:

i. when the symbols $R_1$ each represent an alkali metal atom,
by the action of carbon disulphide in the presence of an alkali metal alkoxide on an acetylpyrazine of the general formula:

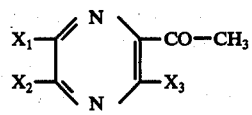

wherein $X_1$, $X_2$ and $X_3$ are as hereinbefore defined. Generally the reaction is effected in an anhydrous organic solvent, for example benzene or toluene, at a temperature of about 20° C.

ii. when the symbols $R_1$ each represent a hydrogen atom, by hydrolysis of a corresponding compound of that formula in which each of the symbols $R_1$ represent an alkali metal atom, in an acid medium. Generally aqueous hydrochloric acid is employed at a temperature of about 20° C.

iii. when the symbols $R_1$ each represent an alkyl radical containing 1 to 4 carbon atoms or together form an alkylene radical containing 2 to 4 L carbon atoms;

a. when the symbols $R_1$ each represent an alkyl radical, by the action of a reactive ester of the general formula:

$R_2—Z$ (V)

wherein $R_2$ represents an alkyl radical containing 1 to 4 carbon atoms and Z represents a halogen atom or the acid residue of a sulphuric or sulphonic ester, or b. when the symbols $R_1$ together form an alkylene radical, by reaction of a reactive diester of the general formula:

$Z—A—Z$ (VI)

wherein the symbols Z are as hereinbefore defined and A represents an alkylene radical containing 2 to 4 carbon atoms, with a pyrazine derivative of general formula II in which T is of formula IIIb, and the symbols $R_1$ each represent an alkali metal atom, optionally prepared in situ.

The reaction is generally effected in the presence of an organic solvent, such as an alcohol, preferably methanol, at a temperature between 20° C. and the boiling temperature of the reaction mixture.

The acetylpyrazines of general formula IV can be obtained by application of the method described by S. Kushner et al, J. Amer. Chem. Soc., 74, 3617 (1952).

According to a further feature of the present invention, the 1,2-dithiole derivatives of general formula I, wherein Y represents an oxygen atom [i.e. the compounds of general formula II in which T is of formula IIIc], are obtained by one of the following processes:

1. by the action of mercuric acetate on a 1,2-dithiole derivative of general formula I in which Y represents a sulphur atom. Generally the reaction is carried out at a temperature between 50° and 100° C. in an organic solvent such as an acid, in particular acetic acid.

2. by the action of sulphur on a pyrazine derivative of the general formula:

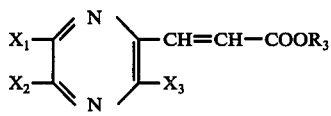

wherein $X_1$, $X_2$ and $X_3$ are as hereinbefore defined and $R_3$ represents an alkyl radical containing 1 to 4 carbon atoms, preferably methyl or ethyl. Generally the reaction is carried out at a temperature between 230° and 260° C. in an organic solvent such as biphenyl.

The pyrazine derivatives of general formula VII can be obtained from a compound of the general formula:

(VIII)

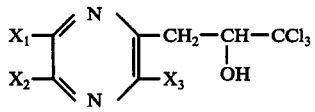

wherein $X_1$, $X_2$ and $X_3$ are as hereinbefore defined, by dehydration followed by alcoholysis. Generally the dehydration is effected by heating a compound of general formula VIII in concentrated sulphuric acid at a temperature of about 100° C. The alcoholysis is effected by treating in situ the product of dehydration with an alcohol containing 1 to 4 carbon atoms at a temperature of about 20° C.

The pyrazine derivatives of general formula VIII can be obtained according to the method described by R. G. Jones et al., J. Amer. Chem. Soc., 72, 3539 (1950).

According to another feature of the invention, the 1,2-dithiole derivatives of general formula I, wherein Y represents a hydroxyimino radical, are obtained by the process which comprises reacting hydroxylamine hydrochloride with a 1,2-dithiole of general formula I in which Y represents a sulphur atom. Generally the reaction is carried out at a temperature between 50° and 100° C in an organic solvent such as an alcohol, preferably methanol.

The 1,2-dithiole derivatives of general formula I obtained by the aforedescribed processes can be purified by physical methods such as crystallisation or chromatography.

The 1,2-dithiole derivatives of general formula I possess useful chemotherapeutic properties. They are particularly interesting as antibilharzial agents and they also possess an anti-amoebic activity. They show moreover a very low toxicity. When administered orally to mice they are non-toxic at doses in the region of or greater than 1,000 mg./kg. animal body weight.

Preferred compounds of the present invention are those 1,2-dithiole derivatives of general formula I in which Y represents a sulphur atom, and more especially those compounds in which the symbols $X_1$, $X_2$ and $X_3$ are the same or different and each represents a hydrogen atom or a methyl or methoxy group. Of outstanding importance is the compound of general formula I wherein the symbols $X_1$, $X_2$ and $X_3$ each represent a hydrogen atom and Y represents a sulphur atom:

its antibilharzial activity is manifest in the mouse infested with Schistosoma mansoni at doses between 500 and 1,000 mg./kg. per day during five days by oral administration and at doses between 125 and 250 mg./kg. animal body weight per day during five days by subcutaneous administration, and in the monkey [Maccaca mulatta (var. rhesus)] at doses of about 100 mg./kg. animal body weight per day for 5 days by oral administration and at doses lower than or equal to 20 mg./kg. animal body weight per day during 5 days by intramuscular administration:

its anti-amoebic activity is manifest against intestinal amoebiasis in the young rat at doses between 200 and 500 mg./kg. animal body weight per day during five days by oral administration, and against hepatic amoebiasis of hamsters due to Entamoeba histolytica at doses greater than 250 mg./kg. animal body weight per day during five days by oral administration.

The other 1,2-dithiole derivatives of general formula I possess to a lesser extent the same properties.

The following Examples illustrate the preparation of 1,2-dithiole derivatives of the present invention.

EXAMPLE 1

Ethyl 3-(pyrazin-2-yl)-3-oxopropionate (97 g.) is added over the course of 5 minutes to a boiling solution of phosphorus pentasulphide (122 g.) in anhydrous pyridine (1,220 cc.). Heating under reflux is continued for one hour after the end of the addition and the reaction mixture is then cooled to a temperature of about 60° C. and poured into distilled water (12,000 cc.). A dark chestnut-coloured suspension is obtained, which is left to stand for 18 hours at a temperature of about 20° C. The insoluble product is filtered off and then washed with distilled water (2 × 200 cc.). After drying, a dark brown product (54.6 g.) is obtained, which is stirred for 1 hour in refluxing 1,2-dichloroethane (1,300 cc.). The boiling suspension is filtered and a product crystallises out on cooling. This product is filtered off and then washed with 1,2-dichloroethane (3 × 30 cc.). After drying, 5-(pyrazin-2-yl)-1,2-dithiole-3-thione (15.3 g.), melting at 196° C., is obtained.

EXAMPLE 2

3,3-bis-Methylthio-1-(pyrazin-2-yl)-prop-2-en-1-one (2.26 g.) is added in the course of about one minute to a boiling suspension of phosphorus pentasulphide (7.1 g.) in anhydrous xylene (140 cc.). Heating under reflux is continued for one hour after the end of the addition, and the reaction mixture is then cooled to a temperature of about 20° C. An insoluble product is filtered off and washed with 1,2-dichloroethane (200 cc.). The filtrate is concentrated to dryness under reduced pressure and the residue obtained is taken up in 1,2-dichloroethane (100 cc.). An insoluble product is filtered off and washed with 1,2-dichloroethane (4 × 50 cc.). The filtrate is extracted successively with a 10% aqueous sodium carbonate solution (100 cc.) and with water (2 × 100 cc.) and is then dried over magnesium sulphate. After filtration of the dried solution, and concentration to dryness under reduced pressure (30 mm Hg), the residue obtained is suspended in carbon disulphide (50 cc.). The insoluble product is filtered off and taken up in boiling 1,2-dichloroethane (25 cc.). The boiling suspension is filtered and then cooled. A product precipitates and is filtered off and then washed with 1,2-dichloroethane (2 × 2 cc.). After drying, 5-(pyrazin-2-yl)-1,2-dithiole-3-thione (0.36 g.) melting at 196° C. is obtained.

3,3-bis-Methylthio-1-(pyrazin-2-yl)-prop-2en-1-one can be prepared in the following manner:

A solution of tertiary butyl alcohol (11.1 g.) in anhydrous toluene (15 cc.) is added over the course of 45 minutes, at a temperature of about 80° C., to a suspension of sodium hydride (50% dispersion in mineral oil) (7.2 g.) in anhydrous toluene (135 cc.). Heating at 80° C. is continued for one hour after the end of the addition and the suspension obtained is then cooled to a temperature of about 35° C. A solution of 2-acetylpyrazine (9.16 g.) and carbon disulphide (5.7 g.) in anhydrous toluene (50 cc.) is then added to the reaction mixture. The reaction mixture is then stirred at a temperature of about 25° C. for 10 hours, after which an insoluble material is filtered off and washed with diisopropyl ether (2 × 50 cc.). After drying, this solid is dissolved in methanol (500 cc.) and methyl iodide (21.3 g.) is added over the course of about one minute, at a temperature of about 40° C. After the end of the addition, the reaction mixture is heated under reflux for 7 hours. After cooling to a temperature of about 25° C., the reaction mixture is poured into water (800 cc.). The insoluble product is filtered off and washed with water (3 × 50 cc.). After drying, a product (6.2 g.) is obtained which after recrystallisation from ethanol (400 cc.) gives 3,3-bis-methylthio-1-(pyrazin-2-yl)-prop-2-en-1-one (1.8 g.) melting at 155° C.

EXAMPLE 3

Following the procedure of Example 1, but starting from ethyl 3-(5,6-dimethylpyrazin-2-yl)-3-oxopropionate (33 g.) and phosphorus pentasulphide (36.4 g.) in pyridine (364 cc.), 5-(5,6-dimethylpyrazin-2-yl)-1,2-dithiole-3-thione (11.3 g.), melting at 205° C., is obtained after recrystallisation from 1,2-dichloroethane.

Ethyl 3-(5,6-dimethylpyrazin-2-yl)-3-oxopropionate can be prepared in the following manner:

A suspension of dry sodium ethoxide (obtained from sodium; 12.7 g.) in anhydrous toluene (200 cc.) is prepared. This suspension is heated to a temperature of about 80° C. and a solution of ethyl 5,6-dimethylpyrazine-2-carboxylate (63 g.) in anhydrous ethyl acetate (104 g.) is added thereto over the course of 1 hour. After the end of the addition, the reaction mixture is heated under reflux for 4 hours and is then cooled to a temperature of about 20° C. and poured into water (1,600 cc.). An insoluble material is filtered off and the organic phase of the filtrate is separated off by decantation. The insoluble material is washed further with water (4 × 400 cc.) and the aqueous filtrates are subsequently used to extract the initial organic phase. The aqueous extracts are recombined, washed with methylene chloride (400 cc.) and then acidified to pH 4 by adding about 4N hydrochloric acid (72 cc.). An oily product separates out and is extracted with methylene chloride (4 × 400 cc.). The organic phases are combined, dried over sodium sulphate and then evaporated to dryness under reduced pressure. The residue obtained is dissolved in diethyl ether (80 cc.) and the cloudy solution obtained is treated with decolorising charcoal (2 g.), filtered and then evaporated to dryness under reduced pressure. Ethyl 3-(5,6-dimethylpyrazin-2-yl)-3-oxo-propionate (30 g.) is thus obtained in the form of an orange oil.

Ethyl 5,6-dimethylpyrazine-2-carboxylate can be prepared in the following manner:

Concentrated sulphuric acid (43.6 g.) is added to a suspension of 5,6-dimethylpyrazine-2-carboxylic acid (99.4 g.) in ethanol (600 cc.) and the mixture is heated under reflux for 13 hours. A solution is obtained which, after cooling, is poured onto ground ice (360 g.). Methylene chloride (400 cc.), followed by potassium carbonate (300 g.), are then added. The aqueous phase is then separated off by decantation, after which it is extracted with methylene chloride (2 × 100 cc.). The organic phases are combined, dried over sodium sulphate and evaporated to dryness under reduced pressure. The residue obtained is taken up in methylene chloride (300 cc.) and the insoluble product is filtered off. The filtrate is again dried over sodium sulphate in the presence of decolorising charcoal, filtered and then evaporated to dryness under reduced pressure. This gives ethyl 5,6-dimethylpyrazine-2-carboxylate (95 g.) in the form of an orange oil.

5,6-Dimethylpyrazine-2-carboxylic acid can be prepared in the following manner:

A suspension of 5,6-dimethylpyrazine-2,3-dicarboxylic acid (110 g.) in 1,2-dichlorobenzene (330 cc.) is heated at a temperature of about 170° C. until the evolution of gas ceases. The reaction mixture is then cooled to a temperature of about 20° C., after which the insoluble product is filtered off and washed with diisopropyl ether (6 × 25 cc.). After drying, 5,6-dimethylpyrazine-2-carboxylic acid (66.4 g.), melting at 187° C., is obtained.

5,6-Dimethylpyrazine-2,3-dicarboxylic acid can be prepared in accordance with the method described by L. E. Hinkel et al., J. Chem. Soc., 1,432 (1937).

EXAMPLE 4

A suspension of phosphorus pentasulphide (2.2 g.) and of ethyl 3-(3-methylpyrazin-2-yl)-3-oxopropionate (1.3 g.) in toluene (25 cc.) is heated for 1 hour at a temperature of about 110° C. The insoluble residue is then filtered off. The toluene filtrate, cooled to a temperature of about 20° C., is washed with a saturated aqueous sodium bicarbonate solution (15 cc.), dried over sodium sulphate, filtered and evaporated to dryness under reduced pressure.

The residue obtained is then dissolved in methylene chloride (30 cc.) and the resulting solution is filtered over silica gel (20 g.) contained in a column of 1.7 cm. diameter. The column is eluted with pure methylene chloride (150 cc.) and the eluate obtained is discarded. Thereafter the column is again eluted with pure methylene chloride (120 cc.). The corresponding eluate is concentrated to dryness under reduced pressure. The solid residue thus obtained is washed with diethyl ether (4 cc) and 5-(3-methylpyrazin-2-yl)-1,2-dithiole-3-thione (0.008 g.), melting at 165° C., is obtained.

Ethyl 3-(3-methylpyrazin-2yl)-3-oxopropionate can be prepared by adding a solution of 2-ethoxycarbonyl-3-methylpyrazine (1.5 g.) and of ethyl acetate (2.4 g.) in anhydrous toluene (5 cc.), at a temperature of about 20° C., over the course of 5 minutes to a suspension of sodium hydride (50% dispersion in mineral oil) (0.73 g.) in anhydrous toluene (30 cc.) and ethanol (0.2 cc.). The reaction mixture is then heated for 4 hours at a temperature of about 105° C. After cooling to a temperature of about 20° C., water (150 cc.) is added. The aqueous solution is acidified to pH 5 by adding a sufficient amount of 4N hydrochloric acid. The aqueous phase is extracted with ethyl acetate (200 cc.) and the organic phase is dried over sodium sulphate and filtered. After evaporation to dryness under reduced pressure, ethyl 3-(3-methylpyrazin-2-yl)-3-oxopropionate (1.3 g.) is obtained in the form of a yellow oil.

2-Ethoxycarbonyl-3-methylpyrazine can be prepared in accordance with the method described by P. Mathias et al., J. Med. Chem. 13, 77 (1970).

EXAMPLE 5

Following the procedure of Example 1, but starting from methyl 3-(6-methoxypyrazin-2-yl)-3-oxo-propionate (14.7 g.) and phosphorus pentasulphide (17.1 g.) in pyridine (147 cc.), a product (7.5 g.) melting at 149° C. is obtained, which is dissolved in methylene chloride (150 cc.). The solution obtained is filtered over silica gel (150 g.) contained in a column of 3 cm. diameter. The column is eluted with methylene chloride (600 cc.) and the eluate obtained is discarded. There-after the column is again eluted with methylene chloride (750 cc.) and the corresponding eluate is evaporated to dryness under reduced pressure. After recrystallisation of the residue obtained from acetonitrile (155 cc.), 5-(6-methoxypyrazin-2-yl)-1,2-dithiole-3-thione (5.2 g.), melting at 152° C., is obtained.

Methyl 3-(6-methoxypyrazin-2-yl)-3-oxopropionate can be prepared by adding a solution of 6-methoxy-2-methoxy carbonylpyrazine (37 g.) and methyl acetate (27.6 g.) in anhydrous toluene (100 cc.) to a suspension of sodium methoxide (19 g.) in anhydrous toluene (220 cc.). The reaction mixture is then heated under reflux for 35 minutes. After cooling, it is poured into water (1,000 cc.) and the organic layer is separated off by decantation and then washed with water (250 cc.). The combined aqueous layers are washed by decantation with diethyl ether (250 cc.) and then acidified to pH 4 with 4N hydrochloric acid (35 cc.). The product which separates out is extracted with methylene chloride (3 × 250 cc.) and the organic solution obtained is dried over sodium sulphate in the presence of decolorising charcoal. After filtration, this solution is evaporated to dryness under reduced pressure. Methyl 3-(6-methoxypyrazin-2-yl)-3-oxopropionate (14 g.), melting at about 66° C., is thus obtained.

6-Methoxy-2-methoxycarbonylpyrazine can be prepared by adding a solution of sodium methoxide (9 g.) in anhydrous methanol (80 cc.) to a solution of 6-chloro-2-methoxycarbonylpyrazine (26.3 g.) in anhydrous methanol (143 cc.). Thereafter the reaction mixture is stirred for 2 hours at a temperature of about 25° C., and is then evaporated to dryness under reduced pressure. The residue obtained is treated with methylene chloride (300 cc.) and the insoluble product is filtered off. The filtrate obtained is treated with decolorising charcoal in the presence of sodium sulphate, filtered and evaporated to dryness under reduced pressure. 6-Methoxy-2-methoxycarbonylpyrazine (19 g.), melting at 73° C., is thus obtained.

6-Chloro-2-methoxycarbonylpyrazine can be prepared by adding 1-oxo-3-methoxycarbonylpyrazine (60.3 g.) over the course of 25 minutes to phosphorus oxychloride (420 cc.) at a temperature of about 50° C. After cooling, the reaction mixture is evaporated to dryness under reduced pressure and the residual oil is poured onto crushed ice (840 g.). The aqueous phase obtained is extracted in 5 stages with methylene chloride (1,000 cc.) The combined organic extracts are dried over sodium sulphate, filtered and evaporated to dryness under reduced pressure. 6-Chloro-2-methoxycarbonylpyrazine (63.5 g.) is thus obtained in the form of a yellow oil.

1-Oxo-3-methoxycarbonylpyrazine can be prepared by adding a solution of methyl pyrazine-2-carboxylate (138 g.) in chloroform (800 cc.) to a solution of metachloroperbenzoic acid (202 g.) in chloroform (3,300 cc.). The reaction mixture is then stirred for 7 days at a temperature of about 25° C. The insoluble product which forms is filtered off and the filtrate is washed by decantation with a 5% (w/v) strength aqueous sodium bicarbonate solution (2,500 cc.) The organic layer is then dried over sodium sulphate, filtered and evaporated to dryness under reduced pressure. Recrystallisation of the residue obtained from methanol (1,350 cc.) gives 1-oxo-3-methoxycarbonylpyrazine (61 g.) melting at 172° C.

EXAMPLE 6

Following the procedure of Example 1, but starting from ethyl 3-(5-methylpyrazin-2yl)-3-oxo-propionate (21.9 g.) and phosphorus pentasulphide (25.8 g.) in pyridine (258 cc.), and recrystallizing the product obtained from 1,2-dichloroethane (80 cc.), 5-(5-methylpyrazin-2-yl)-1,2-dithiole-3-thione (3.6 g.), melting at 192° C., is obtained.

Ethyl 3-(5-methylpyrazin-2-yl)-3-oxopropionate can be prepared by reaction of ethyl acetate with 5-methyl-2-ethoxycarbonylpyrazine in toluene in the presence of sodium ethoxide at a temperature of about 80° C. for 4 hours.

2-Ethoxycarbonyl-5-methylpyrazine can be prepared by reaction of 5-methylpyrazine-2-carboxylic acid with excess ethanol at the reflux temperature for 13 hours, in the presence of concentrated sulphuric acid.

5-Methylpyrazine-2-carboxylic acid can be prepared in accordance with the method described in W. Schwaiger et al., Rec. Trav. Chim. Pays-Bas 91, 1,175 (1972).

EXAMPLE 7

A suspension of 5-(pyrazin-2-yl)-1,2-dithiole-3-thione (21.33 g.) in acetic acid (100 cc.) is heated at a temperature of about 75° C. Mercuric acetate (47.71 g.) is then added and the grey suspension is heated for 1 hour at a temperature of about 95° C. After cooling to a temperature of about 20° C., the insoluble matter is filtered off and is washed with acetic acid (3 × 100 cc.). The filtrate and the wash liquors are combined and are concentrated to dryness under reduced pressure. The solid residue obtained is taken up in water (400 cc.). The insoluble matter is filtered off and then washed with water (3 × 100 cc.), ethanol (100 cc.) and finally methylene chloride (4 × 250 cc.). The combined methylene chloride filtrate is evaporated to dryness under reduced pressure. After recrystallisation of the residue from 1,2-dichloroethane (40 cc.), 5-pyrazin-2-yl)-1,2-dithiole-3-one (3.6 g.), melting at 184° C., is obtained.

EXAMPLE 8

A solution of methyl (pyrazin-2-yl)acrylate (2 g.) and sulphur (1 g.) in biphenyl (10 g.) is heated at 230° C. whilst stirring. After one hour, a further 1 g. of sulphur is added and the heating is continued for 20 minutes. The black solution obtained crystallises on cooling and the product is taken up in chloroform (80 cc.) and treated with decolorising charcoal (1 g.). After filtration, the solvent is evaporated under reduced pressure (30 mm Hg). The residue is taken up in diisopropyl ether (80 cc.) and the liquid phase is filtered over a column containing neutral alumina (100 g.). The column is eluted with diisopropyl ether (2,000 cc.) and then with a mixture (800 cc.) of diisopropyl ether and ethyl acetate (70:30 by volume); after concentration of the last eluate under reduced pressure (30 mm Hg), a partially crystalline residue (0.42 g.) is obtained. This residue is taken up in diisopropyl ether (10 cc.) and the solid is filtered off and washed with diisopropyl ether (2 × 10 cc.).

5-(Pyrazin-2-yl)-1,2-dithiole-3-one (0.18 g.), melting at 181° C., is thus obtained.

Methyl (pyrazin-2-yl)acrylate can be prepared as follows:

A solution of 2-(pyrazin-2-yl)-1-trichloromethylethanol (10.7 g.) in sulphuric acid ($d = 1.83$; 40 cc.) is heated for 1 hour at 90° C. After the evolution of gas has ceased and the mixture has been cooled, the black solution thus obtained is poured carefully into anhydrous methanol (50 cc.) (The temperature rises to 60° C. by the end of the addition), and the whole is then left at 20° C. for 16 hours. The methanol is evaporated under reduced pressure (30 mm Hg) and the residue is taken up in a mixture of ice (100 g.) and distilled water (100 cc.). The aqueous solution is extracted with methylene chloride (3 × 150 cc.); the organic phases are combined, dried over magnesium sulphate and concentrated to dryness under reduced pressure (30 mm Hg). Methyl (pyrazin-2-yl)acrylate (5.7 g.) melting at 92° C. is thus obtained. After recrystallisation from diisopropyl ether, the product melts at 96° C.

2-(Pyrazin-2-yl)-1-trichloromethyl-ethanol can be prepared as described by R. G. Jones et al., J. Amer. Chem. Soc., 72, 3,539 (1950).

EXAMPLE 9

A mixture of 5-(pyrazin-2-yl)-1,2-dithiole-3-one (2 g.) and phosphorus pentasulphide (2.3 g.) in dioxan (35 cc.) is heated for 15 minutes at 100° C., whilst stirring. The red suspension obtained is diluted whilst hot with acetonitrile (35 cc.). The solution is decanted and the precipitate obtained is taken up with a hot mixture (2 × 50 cc.) of dioxan and acetonitrile (50:50 by volume). The combined organic phases are filtered hot, diluted with distilled water (250 cc.), and the requisite amount of a 4N aqueous ammonia solution to adjust the pH to 7. The brown precipitate formed is filtered off, washed with distilled water (2 × 25 cc.) and then with diethyl ether (2 × 10 cc.) and dried. 5-(Pyrazin-2-yl)-1,2-dithiole-3-thione (1.87 g.) melting at 200°–201° C. is thus obtained.

EXAMPLE 10

A suspension of 5-(pyrazin-2-yl)-1,2-dithiole-3-thione (31.85 g.) in methanol (1,400 cc.) is heated at a temperature of about 65° C. Hydroxylamine hydrochloride (24 g.), followed by sodium acetate (35 g.) dissolved in water (75 cc.), are then added. The reaction mixture is then heated for 3 hours at a temperature of about 65° C. After cooling to a temperature of about 20° C., the insoluble product is filtered off and is then washed with methanol (4 × 100 cc.) and with carbon disulphide (4 × 100 cc.). The product is dissolved in dimethylformamide (300 cc.) at 100° C. and is then reprecipitated by adding water (600 cc.). After filtration and drying, 3-hydroxyimino-5-(pyrazin-2-yl)-1,2-dithiole (23 g.) melting at 262° C. is obtained.

The present invention includes within its scope pharmaceutical compositions comprising, as active ingredient, at least one of the compounds of general formula I in association with a pharmaceutical carrier or coating. The invention includes especially such preparations made up for oral, parenteral or rectal administration.

Solid compositions for oral administration include tablets, pills, powders and granules. In such solid compositions the active compound is admixed with at least one inert diluent such as sucrose, lactose or starch. The compositions may also comprise, as is normal practice, additional substances other than inert diluents, e.g. lubricating agents, such as magnesium stearate. Liquid compositions for oral administration include pharmaceutically-acceptable emulsions, solutions, suspensions, syrups, and elixirs containing inert diluents commonly used in the art, such as water or liquid paraffin. Besides inert diluents such compositions may also comprise adjuvants, such as wetting, emulsifying and suspending agents, and sweetening, flavouring and aromatizing agents. The compositions according to the invention, for oral administration, also include capsules of absorbable material such as gelatin containing the active substance with or without the addition of diluents or excipients.

Preparations according to the invention for parenteral administration include sterile aqueous or non-aqueous solutions, suspensions or emulsions. Examples of non-aqueous solvents or vehicles are propylene glycol, polyethylene glycol, vegetable oils such as olive oil, and injectable organic esters such as ethyl oleate. These compositions may also contain adjuvants such as preserving, wetting, emulsifying and dispersing agents. They may be sterilized by, for example, filtration through a bacteria-retaining filter, by incorporation in the compositions of sterilizing agents, by irradiation, or by heating. They may also be manufactured in the form of sterile solid compositions, which can be dissolved in sterile water or some other sterile injectable medium immediately before use.

Compositions for rectal administration are suppositories which contain, in addition to the active substance, excipients such as cacao butter or a suitable wax base.

The percentage of active ingredient in the compositions of the invention may be varied, it being necessary that it should constitute a proportion such that a suitable dosage shall be obtained. The dosage depends on the desired therapeutic effect, on the route of administration and on the duration of the treatment. The compositions are particularly useful in human therapy in the treatment of bilharziasis and amoebiasis. In human therapy the compositions when administered orally to an adult should generally give doses between 25 mg. and 100 mg. of active substance per day; when administered parenterally the compositions should give doses between 5 and 25 mg./kg. of active substance per day. In general the physician will decide the posology considered appropriate, taking into account the age and weight and other factors intrinsic to the patient being treated.

The following Example illustrates pharmaceutical compositions according to the invention.

EXAMPLE 11

Tablets containing 500 mg. of active product and having the following composition are prepared in accordance with the usual technique:

| | |
|---|---|
| 5-(pyrazin-2-yl)-1,2-dithiole-3-thione | 500 mg. |
| wheat starch | 150 mg. |
| precipitated silica | 40 mg. |
| magnesium stearate | 10 mg. |

We claim:

1. A 1,2-dithiole derivative of the formula:

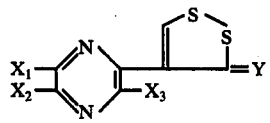

wherein $X_1$, $X_2$ and $X_3$ represent hydrogen, alkyl of 1 through 4 carbon atoms or alkoxy of 1 through 4 carbon atoms, at least one of $X_1$, $X_2$ and $X_3$ representing hydrogen, and Y represents sulphur or oxygen or the hydroxyimino radical.

2. A 1,2-dithiole derivative according to claim 1 wherein Y represents sulphur.

3. A 1,2-dithiole derivative according to claim 1 wherein $X_1$, $X_2$ and $X_3$ represent hydrogen, methyl or methoxy, and Y represents sulphur or oxygen or the hydroxyimino radical.

4. A 1,2-dithiole derivative according to claim 1 wherein $X_1$, $X_2$ and $X_3$ represent hydrogen, methyl or methoxy, and Y represents sulphur.

5. 5-(Pyrazin-2-yl)-1,2-dithiole-3-thione.
6. 5-(5,6-Dimethylpyrazin-2-yl)-1,2-dithiole-3-thione.
7. 5-(3-Methylpyrazin-2-yl)-1,2-dithiole-3-thione.
8. 5-(6-Methoxypyrazin-2-yl)-1,2-dithiole-3-thione.
9. 5-(5-Methylpyrazin-2-yl)-1,2-dithiole-3-thione.
10. 5-(Pyrazin-2-yl)-1,2-dithiole-3-one.
11. 3-Hydroxyimino-5-(pyrazin-2-yl)-1,2-dithiole.

12. A pharmaceutical composition useful in the treatment of bilharziasis and amoebiasis which comprises a therapeutically active amount of a 1,2-dithiole derivative as claimed in claim 1 in association with a significant amount of a compatible pharmaceutically acceptable carrier.

* * * * *